Sept. 3, 1963 M. VAN RENSSELAER Plant Pat. 2,277
PISTACIA CHINENSIS TREE
Filed June 7, 1962 2 Sheets-Sheet 1
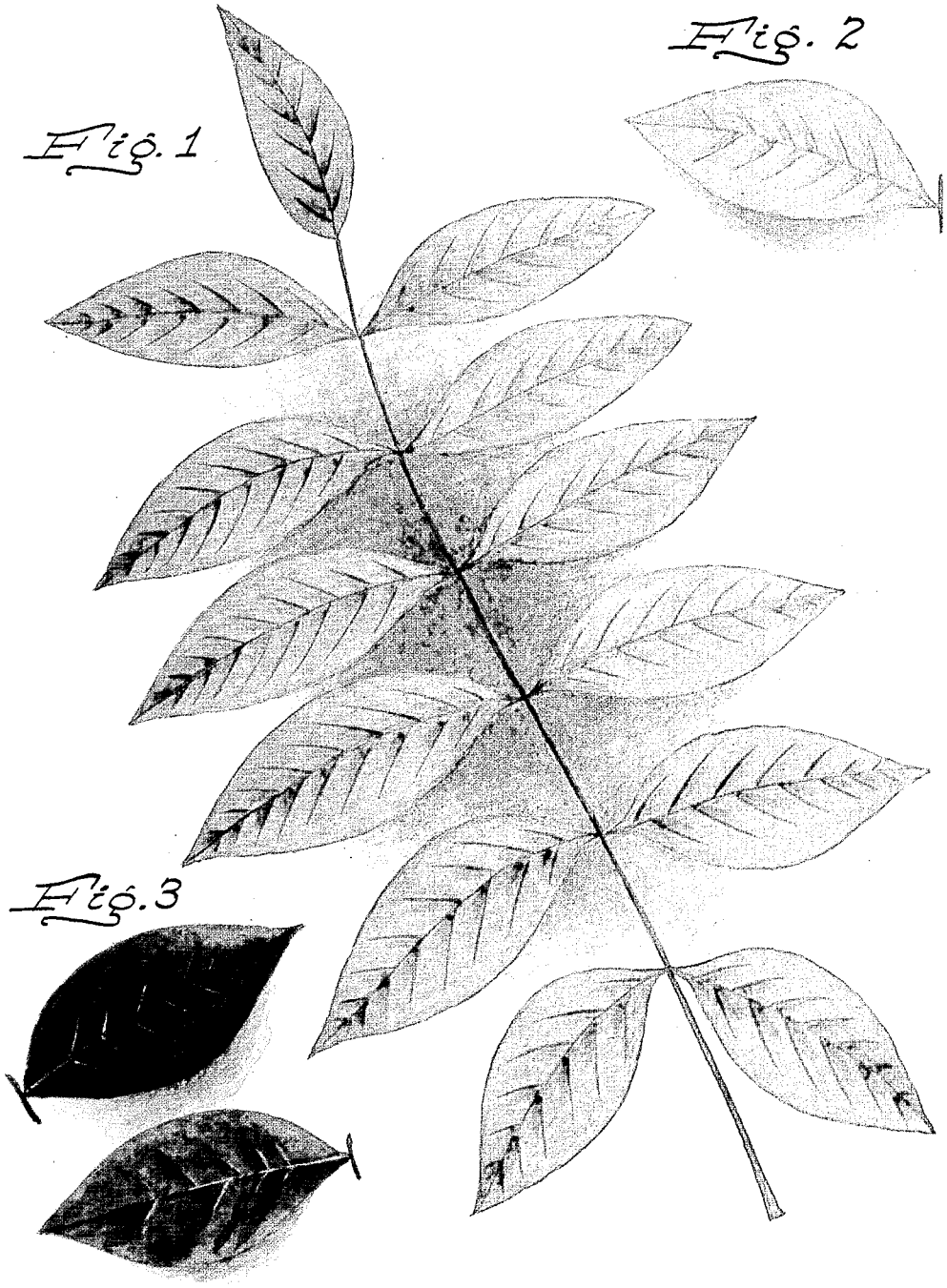
WITNESS
Addison E. Avery
INVENTOR
Maunsell Van Rensselaer
Webster & Webster
ATTYS.

United States Patent Office

Plant Pat. 2,277
Patented Sept. 3, 1963

2,277

*PISTACIA CHINENSIS* TREE

Maunsell Van Rensselaer, Saratoga, Calif., assignor to Saratoga Horticultural Foundation, Saratoga, Calif., a nonprofit corporation of California Filed June 7, 1962, Ser. No. 200,901
1 Claim. (Cl. Plt.—30)

This discovery relates to a new and distinct variety of *Pistacia chinensis* tree having certain characteristics, as hereinafter described, which make the variety especially desirable for ornamental purposes.

The original tree of the present variety was discovered by me growing, as a mature tree, in a cultivated or domestic garden in Los Altos, California; such parent tree—upon close and continuing observation—having been recognized by me, in comparison to the common and well known species of *Pistacia chinensis,* as botanically distinctive in several advantageous respects.

The term "species" as used hereinafter shall be deemed to embrace the *Pistacia chinensis* as known prior to my present discovery.

After such discovery of the present variety of *Pistacia chinensis,* and the recognition of its distinctiveness, asexual reproduction was accomplished by me at the Saratoga Horticultural Foundation, Saratoga, California, by grafting scions, obtained from the original tree, on seedling-grown root stock of the *Pistacia chinensis* species. All such asexual reproductions were found to hold true to the original tree.

In the drawings:

FIG. 1 is an elevation of a leaf of the variety, shown in autumn color.

FIG. 2 is an underside view of one of the leaflets, also in autumn color.

FIG. 3 is a composite view showing two leaflets in spring-summer color; the uppermost leaflet showing the top side and the lowermost leaflet showing the under side.

Figure 4:
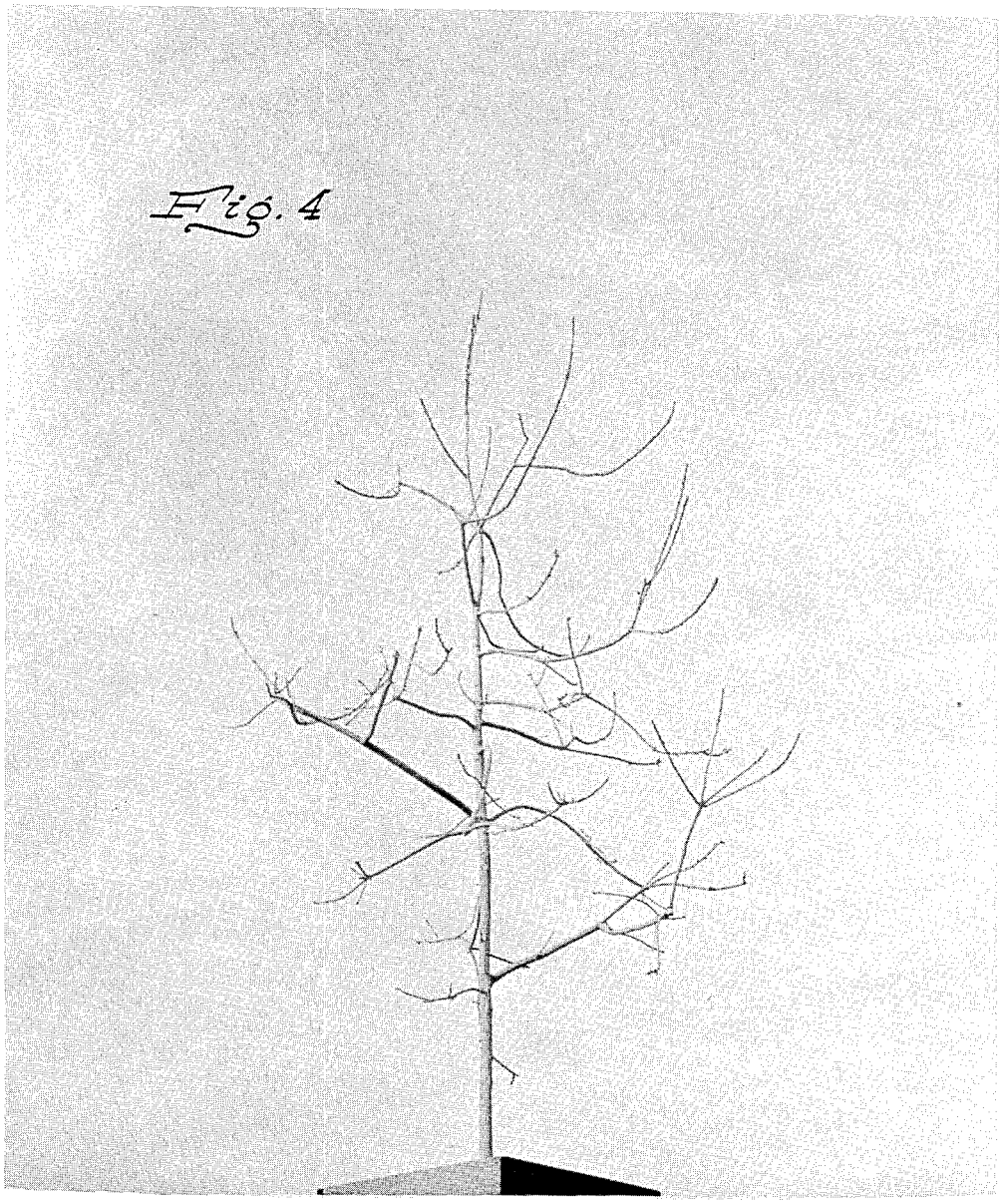
FIG. 4 is a view of a relatively young tree before foliation.

Referring now to the botanical details of the present new and distinct variety of *Pistacia chinensis* tree, the following is an outline description thereof; all major color plate identifications being by reference to Maerz and Paul Dictionary of Color.

Family: Anacardiaceae.
Parentage: Unknown.
Type: Seedling.
Tree: Deciduous; approximately 35 feet in height, with a dense symmetrical crown approximately 30 feet in diameter; strong, well crotched branches; branchlets puberulent; hardiness zone VIII.
Leaves: Alternate, odd or even pinnate, average 6 to 10 inches in length; leaflets average 8 to 15 in number, short stalked, entire, lanceolate, average 7/16 to 1 5/16 inches in width, average 1 7/8 to 3 5/16 inches in length, oblique, puberulent when young but soon glabrous or nearly so; petiole and rachis puberulent.
Color of foliage:
*Spring-Summer.*—Top side—Green (22–L–6). Under side—Lighter Green (20–L–7).
*Autumn.*—Top side—Cardinal Red (4–K–6, shading to 6–H–6). Under side—Lighter Red (4–I–5).
Flowers: Bears staminate flowers only; small in dense panicles; average 2 to 3 inches in length.

The following are noteworthy and distinctive features of the present variety of *Pistacia chinensis*:

*Absence of Fruit*

The trees of this variety bear only staminate flowers, hence produce no fruit. The fruit as borne on pistillate trees of the species is an objectionable feature when the trees are planted for ornametnal purposes; this because the countless fruit that falls on the sidewalk, street, patio, or lawn is messy and slippery and thus must be recurringly cleaned up over a period of several months each year. Additionally, the heavy crop of fruit on pistillate trees of the species weighs down the branches to such an extent that the tree commonly has a sprawly, somewhat open crown. These objects are wholly eliminated in the staminate variety of *Pistacia chinensis* herein claimed.

*Structure of Trunk and Crown*

The original tree of this variety had a handsome, dense, symmetrical crown and a straight, sturdy trunk with strong, well spaced and well crotched branches. Close examination by me of asexually propagated trees of the present variety has disclosed an inherent ability of such trees to grow with the same desirable balance between trunk and branches. Further, a comparison of the branching habit of the present variety with seedling-grown trees of the species, all of the same age, yields the following information:

The growth of lateral branches, which obviously is a fundamental requirement for proper crown development, is almost non-existent on most seedling-grown trees of the species. When branching finally occurs on trees that are then tall and spindly, the branches are usually far apart and poorly spaced. Emphasis on terminal growth appears to be characteristic of young trees of the species grown from seed. This results in light caliper of trunk, with the need for a long period of stake support after planting.

In contra-distinction, the formation of lateral branches on trees of the present variety, which were asexually propagated by grafting scions from the mature original tree (such scions possessing physiological maturity), is far superior to the branch formation on seedling-grown trees, both in number of branches and position of branches.

More particularly, observations over a period of several years have led to the conclusion that the branching characteristics of the variety herein claimed are superior to seedling-grown stock, and to any other known clonal form of the species, because:

(*a*) The heavy caliper of the terminal growth, with moderate terminal vigor, provides full development of the terminal bud, including 3 or 4 buds in the terminal zone; such buds developing into strong and regularly-spaced side branches.

(*b*) One or more sets of well spaced laterals are produced annually with relatively short internodes.

(*c*) The heavy caliper of the terminal growth results in heavy caliper throughout the trunk, which makes it possible to eliminate the supporting stake within two years after initial planting.

The foregoing elements of crown and trunk development predominate as a permanent growth pattern of the present variety; thus providing a tree of superior structure, especially for ornamental growing.

*Size of Leaves*

The leaves and leaflets of the variety are generally larger, on the average, than those of the species.

*Color*

In the spring and summer the foliage is an attractive green, which foliage in the autumn (October-November) turns to a rich Cardinal Red. As the leaves—i.e. the leaflets—are somewhat translucent, such Cardinal Red autumn color is most vivid when the tree is back-lighted by the sun.

*Desirability*

Because the *Pistacia chinensis* is drought enduring and pest resistant it has—in the past—been in substantial demand. However, as hertofore only seedling-grown nursery stock has been available and, because of wide seedling variation as noted hereinbefore, the performance of the trees proved to be highly unpredictable. This, together with the undesirable bearing of fruit, by pistallate trees has caused the species to generally fall into disfavor, and its popularity is on the wane.

With the introduction of the present variety of *Pistacia chinensis* the performance or characteristics of the trees can be well predicted, and those planting such trees can look forward to:

(1) The total elimination of the problem of fruit.

(2) Sturdy young trees with straight trunks and sufficient caliper to make them free-standing within two years after planting.

(3) Handsome crown structure with well proportioned dimensions.

(4) Strong, well spaced and well crotched branches.

(5) Attractive spring and summer foliage.

(6) Distinctive and vivid rich Cardinal Red autumn foliage.

The variety of *Pistacia chinensis* tree as herein described may vary in slight detail due to climatic and soil conditions under which the variety may be grown; the present description being of the variety as grown at Saratoga, California.

The following is claimed:

A new and distinct variety of *Pistacia chinensis* tree, substantially as shown and described, characterized by a dense symmetrical crown and a straight sturdy trunk with strong well spaced and well crotched branches; by staminate flowers only, with resultant absence of fruit; by leaves larger on the average than those of the species; and by foliage, which is somewhat translucent, of a rich Cardinal Red in autumn color.

No references cited.